(12) United States Patent
Malboobi et al.

(10) Patent No.: US 8,361,956 B2
(45) Date of Patent: Jan. 29, 2013

(54) RECOMBINANT APASES NUCLEIC ACID SEQUENCES

(76) Inventors: Mohammad Ali Malboobi, Tehran (IR); Mohammad Reza Sarikhani, Safashahr (IR); Ralf Greiner, Dettenheim (DE)

( * ) Notice: Subject to any disclaimer, the term of this patent is extended or adjusted under 35 U.S.C. 154(b) by 152 days.

(21) Appl. No.: 12/948,810

(22) Filed: Nov. 18, 2010

(65) Prior Publication Data

US 2012/0128825 A1   May 24, 2012

(51) Int. Cl.
*A61K 38/00* (2006.01)
(52) U.S. Cl. ........................................ 514/1.1; 514/21.2
(58) Field of Classification Search .................... 514/1.1, 514/21.2
See application file for complete search history.

(56) References Cited

U.S. PATENT DOCUMENTS 6,720,014 B1 * 4/2004 Short et al. ...................... 426/52

OTHER PUBLICATIONS

Arabinose efflux permease family protein from *Pseudomonas* GM78; NCBI Reference Sequence: ZP_10624800.1; published Jul. 31, 2012.*
Sugar phosphate permease from *Pseudomonas* GM78; NCBI Reference Sequence: ZP_10622620.1; published Jul. 31, 2012.*

* cited by examiner

*Primary Examiner* — Michele K Joike
*Assistant Examiner* — Antonio Galisteo Gonzalez
(74) *Attorney, Agent, or Firm* — Barry Choobin; Choobin & Choobin Consultancy

(57) ABSTRACT

The various embodiments herein provide nucleic acid sequences isolated from *Pseudomonas putida* strain P13 encoding a family of APases including a phytase and a sugar phosphatase which are highly active at a temperature of 60° C. and at a broad range of pH and withstand the harsh conditions of food processing and digestive system of animals. The enzymes are active at a wide temperature range of 20° C. to 75° C. and at a pH of 5. The embodiments also provide a method of production of the APases. The embodiments also provide a method of isolation and cloning of the APases.

10 Claims, 15 Drawing Sheets

ATGGCCTTTCACCCAATCGCCAACGATGACGCCGCTGGTTGCGTCAA

CGTTGCACGCAAATATGCCTGGGTAGTCTTTGCACTGACCTTCGGCC

TGTTGATTTCCGATTACATGTCGCGCCAGGTGCTCAATGCGGTGTTC

CCGCTGCTGAAGGGCGAGTGGGCACTGAGTGATGGCCAGCTTGGCT

TGCTCAGTGGCATTGTCGCCCTGATGGTCGGTCTGCTGACGTTCCCG

CTGTCGCTGATGGCCGACCGTTTCGGCCGGGTCAAGAGCCTGGCGCT

GATGGCGCTACTGTGGAGCCTGGCCACGCTGGGCTGTGCCTTGGCGC

AGGACTACCAACAGATGTTCATCGCGCGCTTCATGGTCGGCGTCGGC

GAAGCCGCCTACGGCAGCGTAGGCATCGCACTGGTTATTTCGGTTTT

CCCGAAACACATGCGCGCCACCCTGGCCAGCGCGTTCATGGCCGGC

GGCTTGTTCGGCGCTGTGCTGGGCATGGCCCTGGGTGGCGCGATCGC

GGCGAAGCTGGGCTGGCGCTGGTCGTTCGCCGGCATGGCGTTGTTCG

GCCTGTGCCTGGCGGTGCTGTACCCGATCATCGTCAAGGAAGCGCGC

AtGCGCCGCAACGTGCGGCGCGGGCCCTGGACAAGGGGGCGCAGG

ACCTGCGCCCGTTGCGCACGCTGTGGTCCAGCCGTTCGGTGGTGGCG

ACCTATGTGGGGCAGTGGTTTGCAGTTGTTCGTCGGCGGGCACGTTG

```
ATGAGCGGATTCCAGAAGGAGCAAACACTAGTGAATATCCAGGTCG
ACAGTACGGTCCTGCAAAACAAGAAAACCTACCTCTACGAGTGGTA
CGTGGTCGGTTTGTGCATGATCGCCTACATCTTTTCATTTGTTGATCG
ACAGATCCTGGCGCTGATGATCGAGCCGATCAAAGCCGACCTGCAG
ATCAGCGACACTCAGTTCAGCCTGCTTCACGGGCTGGCCTTTTCGTT
GTTCTATGCCTTCATGGGCATGCCCATCGCCTATCTGGCGGACCGTT
TCTCCCGGCCGAAAATCATCGCCGTCGGCGTCGTGTTCTGGAGCCTG
GCGACGGCTGCCTGCGGCTTGAGCAAGAACTTCCTGCACATGTTCCT
CGCCCGTATTGGCGTCGGCGTCGGCGAAGCGGCCCTGTCGCCCTCGG
CCTACTCGATGTTCAGCGACATGTTCCCCAAGGAAAAACTCGGCCGC
GCAGTCGGCATCTATTCGATCGGTTCGTTCGTCGGTGGCGGCCTGGC
CTTCCTGGTGGGTGGCTATGTGATCGCCATGCTCAAGGACATGAACA
CCATCGAGGTGGCCTTTCTCGGTGCGATGAAAGCCTGGCAGCTGGCG
TTCTTCATTGTCGGCCTGCCCGGCATCGTGGTCGGCCTGCTGATCTG
GCTCACCGTGCGTAACCCGGCGCGCAAGGGCCTGCAGGTCGATGCG
CAGGGCAGGGCCAGGAAGGTCGGGATGACTGACGGCCTGCGTTTCC
TCGGGCGTCACCGTGCCACCTTCGCCTGCCATTACCTGGGCTTTTCGT
TCTACGCCATGGTGCTGTTCTGCATGATGAGCTGGAGCCCGGCGCTG
TATATCCGCAAGTTCGGCCTGTCGCCGATGGAAGCAGGCTACATGCT
CGGCACCGTACTGCTGTTGGCCAACACCGCCGGGGTGCTGTTCGGTG
GATGGCTCACCGATTACCTGGCCAGGAAAGGACATCAGGATGCCGC
GATGCGCACCGGCGTCATCGGCGCCCTCGGCATGGCGGTGCCAGCC
GTGCTGTTCCCCCAGGCTGATCAACTGTGGCTGTCGGTGACCCTGCT
GGTGCCGGCGATGTTCTTCGCCTCGTTCCCGAAGCCGGCGTCCACGG
CGGCGATGCAGATTCTTGCGCCGAACCAGGTGCGTGCACAGGTCTC
GGCGGTGTTCCTGCTGATCAGCAATTTGCTGGGGTTGGGCCTGGGCA
CCACCTTGGTGGCGCTGTTGACCGACCGCTACTTCGGATCGCCCGCG
GCGGTAGGTTCGTCGATGTCGCTGGTGATCTGTGGGCGTCGGCGTT
GACTGTGCTGCTGCTATGGCACGGCTGCCGCCGTTTCCGCGAAAGCT
ATGCACGGGAGTACCCTGCCCAGGCGTGA
```

FIG.2

MAFHPIANDDAAGCVNVARKYAWVVFALTFGLLISDYMSRQVLNAVF

PLLKGEWALSDGQLGLLSGIVALMVGLLTFPLSLMADRFGRVKSLALM

ALLWSLATLGCALAQDYQQMFIARFMVGVGEAAYGSVGIALVISVFPK

HMRATLASAFMAGGLFGAVLGMALGGAIAAKLGWRWSFAGMALFGL

CLAVLYPIIVKEARIAPQRAARALDKGAQDLRPLRTLWSSRSVVATYVG

QWFAVVRRRAR

FIG.3

MSGFQKEQTLVNIQVDSTVLQNKKTYLYEWYVVGLCMIAYIFSFVDRQ

ILALMIEPIKADLQISDTQFSLLHGLAFSLFYAFMGMPIAYLADRFSRPKII

AVGVVFWSLATAACGLSKNFLHMFLARIGVGVGEAALSPSAYSMFSD

MFPKEKLGRAVGIYSIGSFVGGGLAFLVGGYVIAMLKDMNTIEVAFLG

AMKAWQLAFFIVGLPGIVVGLLIWLTVRNPARKGLQVDAQGRARKVG

MTDGLRFLGRHRATFACHYLGFSFYAMVLFCMMSWSPALYIRKFGLSP

MEAGYMLGTVLLLANTAGVLFGGWLTDYLARKGHQDAAMRTGVIGA

LGMAVPAVLFPQADQLWLSVTLLVPAMFFASFPKPASTAAMQILAPNQ

VRAQVSAVFLLISNLLGLGLGTTLVALLTDRYFGSPAAVGSSMSLVICG

ASALTVLLLWHGCRRFRESYAREYPAQA

FIG.4

SEQUENCE LISTING

```
<160> NUMBER OF SEQ ID NOS: 12

<210> SEQ ID NO 1
<211> LENGTH: 750
<212> TYPE: DNA
<213> ORGANISM: Pseudomonas putida
<220> FEATURE:
<223> OTHER INFORMATION: Pseudomonas putida P13
```

<400> SEQUENCE: 1

```
atggccttc acccaatcgc caacgatgac gccgctggtt gcgtcaacgt tgcacgcaaa      60
tatgcctggg tagtctttgc actgaccttc ggcctgttga tttccgatta catgtcgcgc     120
caggtgctca atgcggtgtt cccgctgctg aagggcgagt gggcactgag tgatggccag     180
cttggcttgc tcagtggcat tgtcgccctg atggtcggtc tgctgacgtt cccgctgtcg     240
ctgatggccg accgtttcgg ccgggtcaag agcctggcgc tgatggcgct actgtggagc     300
ctggccacgc tgggctgtgc cttggcgcag gactaccaac agatgttcat cgcgcgcttc     360
atggtcggcg tcggcgaagc cgcctacggc agcgtaggca tcgcactggt tatttcggtt     420
ttcccgaaac acatgcgcgc caccctggcc agcgcgttca tggccggcgg cttgttcggc     480
gctgtgctgg gcatggccct gggtggcgcg atcgcggcga gctgggctg gcgctggtcg     540
ttcgccggca tggcgttgtt cggcctgtgc ctggcggtgc tgtacccgat catcgtcaag     600
gaagcgcgca ttgcgccgca acgtgcggcg cgggccctgg acaagggggc gcaggacctg     660
cgcccgttgc gcacgctgtg gtccagccgt tcggtggtgg cgacctatgt ggggcagtgg     720
tttgcagttg ttcgtcggcg ggcacgttga                                      750
```

<210> SEQ ID NO 2
<211> LENGTH: 1386
<212> TYPE: DNA
<213> ORGANISM: Pseudomonas putida
<220> FEATURE:
<223> OTHER INFORMATION: Pseudomonas putida P13

<400> SEQUENCE: 2

```
atgagcggat ccagaaagga gcaaacacta gtgaatatcc aggtcgacag tacggtcctg      60
caaaacaaga aacctaccct ctacgagtgg tacgtggtcg gtttgtgcat gatcgcctac     120
atcttttcat tgttgatcg acagatcctg gcgctgatga tcgagccgat caaagccgac     180
ctgcagatca gcgacactca gttcagcctg cttcacgggc tggccttttc gttgttctat     240
gccttcatgg gcatgccat cgcctatctg gcggaccgtt ctcccggcc gaaaatcatc      300
gccgtcggcg tcgtgttctg gagcctggcg acggctgcct gcggcttgag caagaacttc     360
ctgcacatgt tcctcgcccg tattggcgtc ggcgtcggcg aagcggccct gtcgccctcg     420
gcctactcga tgttcagcga catgttcccc aaggaaaaac tcggccgcgc agtcggcatc     480
tattcgatcg gttcgttcgt cggtggcggc ctggccttcc tggtgggtgg ctatgtgatc     540
gccatgctca aggacatgaa caccatcgag gtggcctttc tcggtgcgat gaaagcctgg     600
cagctggcgt tcttcattgt cggcctgccc ggcatcgtgg tcggcctgct gatctggctc     660
accgtgcgta acccggcgcg caagggcctg caggtcgatg cgcagggcag ggccaggaag     720
gtcgggatga ctgacggcct gcgttttcctc gggcgtcacc gtgccacctt cgcctgccat     780
tacctgggct tttcgttcta cgccatggtg ctgttctgca tgatgagctg gagcccggcg     840
ctgtatatcc gcaagttcgg cctgtcgccg atggaagcag gctacatgct cggcaccgta     900
ctgctgttgg ccaacaccgc cggggtgctg ttcggtggat ggctcaccga ttacctggcc     960
aggaaaggac atcaggatgc cgcgatgcgc accggcgtca tcggcgccct cggcatggcg    1020
gtgccagccg tgctgttccc ccaggctgat caactgtggc tgtcggtgac cctgctggtg    1080
ccggcgatgt tcttcgcctc gttcccgaag ccggcgtcca cggcggcgat gcagattctt    1140
gcgccgaacc aggtgcgtgc acaggtctcg gcggtgttcc tgctgatcag caatttgctg    1200
gggttgggcc tgggcaccac cttggtggcg ctgttgaccg accgctactt cggatcgccc    1260
```

```
gcggcggtag gttcgtcgat gtcgctggtg atctgtgggg cgtcggcgtt gactgtgctg    1320
ctgctatggc acggctgccg ccgtttccgc gaaagctatg cacgggagta ccctgcccag    1380
gcgtga                                                                1386
```

<210> SEQ ID NO 3
<211> LENGTH: 249
<212> TYPE: PRT
<213> ORGANISM: Pseudomonas putida
<220> FEATURE:
<223> OTHER INFORMATION: Pseudomonas putida P13

<400> SEQUENCE: 3

```
Met Ala Phe His Pro Ile Ala Asn Asp Asp Ala Ala Gly Cys Val Asn
1               5                   10                  15

Val Ala Arg Lys Tyr Ala Trp Val Val Phe Ala Leu Thr Phe Gly Leu
            20                  25                  30

Leu Ile Ser Asp Tyr Met Ser Arg Gln Val Leu Asn Ala Val Phe Pro
        35                  40                  45

Leu Leu Lys Gly Glu Trp Ala Leu Ser Asp Gly Gln Leu Gly Leu Leu
    50                  55                  60

Ser Gly Ile Val Ala Leu Met Val Gly Leu Leu Thr Phe Pro Leu Ser
65                  70                  75                  80

Leu Met Ala Asp Arg Phe Gly Arg Val Lys Ser Leu Ala Leu Met Ala
                85                  90                  95

Leu Leu Trp Ser Leu Ala Thr Leu Gly Cys Ala Leu Ala Gln Asp Tyr
            100                 105                 110

Gln Gln Met Phe Ile Ala Arg Phe Met Val Gly Val Gly Glu Ala Ala
        115                 120                 125

Tyr Gly Ser Val Gly Ile Ala Leu Val Ile Ser Val Phe Pro Lys His
    130                 135                 140

Met Arg Ala Thr Leu Ala Ser Ala Phe Met Ala Gly Gly Leu Phe Gly
145                 150                 155                 160

Ala Val Leu Gly Met Ala Leu Gly Gly Ala Ile Ala Ala Lys Leu Gly
                165                 170                 175

Trp Arg Trp Ser Phe Ala Gly Met Ala Leu Phe Gly Leu Cys Leu Ala
            180                 185                 190

Val Leu Tyr Pro Ile Ile Val Lys Glu Ala Arg Ile Ala Pro Gln Arg
        195                 200                 205

Ala Ala Arg Ala Leu Asp Lys Gly Ala Gln Asp Leu Arg Pro Leu Arg
    210                 215                 220

Thr Leu Trp Ser Ser Arg Ser Val Val Ala Thr Tyr Val Gly Gln Trp
225                 230                 235                 240

Phe Ala Val Val Arg Arg Ala Arg
                245
```

<210> SEQ ID NO 4
<211> LENGTH: 461
<212> TYPE: PRT
<213> ORGANISM: Pseudomonas putida
<220> FEATURE:
<223> OTHER INFORMATION: Pseudomonas putida P13

<400> SEQUENCE: 4

```
Met Ser Gly Phe Gln Lys Glu Gln Thr Leu Val Asn Ile Gln Val Asp
1               5                   10                  15

Ser Thr Val Leu Gln Asn Lys Lys Thr Tyr Leu Tyr Glu Trp Tyr Val
            20                  25                  30
```

-continued

Val Gly Leu Cys Met Ile Ala Tyr Ile Phe Ser Phe Val Asp Arg Gln
            35                  40                  45

Ile Leu Ala Leu Met Ile Glu Pro Ile Lys Ala Asp Leu Gln Ile Ser
 50                  55                  60

Asp Thr Gln Phe Ser Leu Leu His Gly Leu Ala Phe Ser Leu Phe Tyr
 65                  70                  75                  80

Ala Phe Met Gly Met Pro Ile Ala Tyr Leu Ala Asp Arg Phe Ser Arg
                 85                  90                  95

Pro Lys Ile Ile Ala Val Gly Val Val Phe Trp Ser Leu Ala Thr Ala
                100                 105                 110

Ala Cys Gly Leu Ser Lys Asn Phe Leu His Met Phe Leu Ala Arg Ile
            115                 120                 125

Gly Val Gly Val Gly Glu Ala Ala Leu Ser Pro Ser Ala Tyr Ser Met
130                 135                 140

Phe Ser Asp Met Phe Pro Lys Glu Lys Leu Gly Arg Ala Val Gly Ile
145                 150                 155                 160

Tyr Ser Ile Gly Ser Phe Val Gly Gly Leu Ala Phe Leu Val Gly
                165                 170                 175

Gly Tyr Val Ile Ala Met Leu Lys Asp Met Asn Thr Ile Glu Val Ala
            180                 185                 190

Phe Leu Gly Ala Met Lys Ala Trp Gln Leu Ala Phe Phe Ile Val Gly
            195                 200                 205

Leu Pro Gly Ile Val Val Gly Leu Leu Ile Trp Leu Thr Val Arg Asn
210                 215                 220

Pro Ala Arg Lys Gly Leu Gln Val Asp Ala Gln Gly Arg Ala Arg Lys
225                 230                 235                 240

Val Gly Met Thr Asp Gly Leu Arg Phe Leu Gly Arg His Arg Ala Thr
                245                 250                 255

Phe Ala Cys His Tyr Leu Gly Phe Ser Phe Tyr Ala Met Val Leu Phe
            260                 265                 270

Cys Met Met Ser Trp Ser Pro Ala Leu Tyr Ile Arg Lys Phe Gly Leu
            275                 280                 285

Ser Pro Met Glu Ala Gly Tyr Met Leu Gly Thr Val Leu Leu Leu Ala
            290                 295                 300

Asn Thr Ala Gly Val Leu Phe Gly Gly Trp Leu Thr Asp Tyr Leu Ala
305                 310                 315                 320

Arg Lys Gly His Gln Asp Ala Ala Met Arg Thr Gly Val Ile Gly Ala
                325                 330                 335

Leu Gly Met Ala Val Pro Ala Val Leu Phe Pro Gln Ala Asp Gln Leu
            340                 345                 350

Trp Leu Ser Val Thr Leu Leu Val Pro Ala Met Phe Phe Ala Ser Phe
            355                 360                 365

Pro Lys Pro Ala Ser Thr Ala Ala Met Gln Ile Leu Ala Pro Asn Gln
            370                 375                 380

Val Arg Ala Gln Val Ser Ala Val Phe Leu Leu Ile Ser Asn Leu Leu
385                 390                 395                 400

Gly Leu Gly Leu Gly Thr Thr Leu Val Ala Leu Leu Thr Asp Arg Tyr
                405                 410                 415

Phe Gly Ser Pro Ala Ala Val Gly Ser Ser Met Ser Leu Val Ile Cys
            420                 425                 430

Gly Ala Ser Ala Leu Thr Val Leu Leu Leu Trp His Gly Cys Arg Arg
            435                 440                 445

Phe Arg Glu Ser Tyr Ala Arg Glu Tyr Pro Ala Gln Ala

```
                450         455         460
```

<210> SEQ ID NO 5
<211> LENGTH: 23
<212> TYPE: DNA
<213> ORGANISM: Artificial Sequence
<220> FEATURE:
<223> OTHER INFORMATION: Description of Artificial Sequence: Synthetic
      forward primer for SEQ ID NO:1

<400> SEQUENCE: 5
gaattcatgg cctttcaccc aat                                           23

<210> SEQ ID NO 6
<211> LENGTH: 21
<212> TYPE: DNA
<213> ORGANISM: Artificial Sequence
<220> FEATURE:
<223> OTHER INFORMATION: Description of Artificial Sequence: Synthetic
      reverse primer sequence for SEQ ID NO:1

<400> SEQUENCE: 6
aagctttcaa cgtgcccgcc g                                             21

<210> SEQ ID NO 7
<211> LENGTH: 24
<212> TYPE: DNA
<213> ORGANISM: Artificial Sequence
<220> FEATURE:
<223> OTHER INFORMATION: Description of Artificial Sequence: Synthetic
      forward primer for SEQ ID NO:3

<400> SEQUENCE: 7
gaattcatga gcggattcca gaag                                          24

<210> SEQ ID NO 8
<211> LENGTH: 22
<212> TYPE: DNA
<213> ORGANISM: Artificial Sequence
<220> FEATURE:
<223> OTHER INFORMATION: Description of Artificial Sequence: Synthetic
      reverse primer sequence for SEQ ID NO:3

<400> SEQUENCE: 8
aagctttcac gcctgggcag gg                                            22

<210> SEQ ID NO 9
<211> LENGTH: 8
<212> TYPE: PRT
<213> ORGANISM: Unknown
<220> FEATURE:
<223> OTHER INFORMATION: Description of Unknown: Bacterial
      APase signature motif

<400> SEQUENCE: 9

Gly Ser Tyr Pro Ser Gly His Thr
1               5

<210> SEQ ID NO 10
<211> LENGTH: 12
<212> TYPE: PRT
<213> ORGANISM: Unknown
<220> FEATURE:
<223> OTHER INFORMATION: Description of Unknown: Bacterial
      APase signature motif

<400> SEQUENCE: 10

Phe Asp Ile Asp Asp Thr Val Leu Phe Ser Ser Pro

```
<210> SEQ ID NO 11
<211> LENGTH: 4
<212> TYPE: PRT
<213> ORGANISM: Unknown
<220> FEATURE:
<223> OTHER INFORMATION: Description of Unknown: Bacterial
      NSAP conserved domain

<400> SEQUENCE: 11

Asp Asp Asp Asp
1

<210> SEQ ID NO 12
<211> LENGTH: 7
<212> TYPE: PRT
<213> ORGANISM: Artificial Sequence
<220> FEATURE:
<223> OTHER INFORMATION: Description of Artificial Sequence: Synthetic
      consensus motif
<220> FEATURE:
<221> NAME/KEY: MOD_RES
<222> LOCATION: (4)..(4)
<223> OTHER INFORMATION: Any amino acid
<220> FEATURE:
<221> NAME/KEY: MOD_RES
<222> LOCATION: (6)..(6)
<223> OTHER INFORMATION: Any amino acid

<400> SEQUENCE: 12

Arg His Gly Xaa Arg Xaa Pro
1               5
```

RECOMBINANT APASES NUCLEIC ACID SEQUENCES

SEQUENCE LISTING

The instant application contains a Sequence Listing which has been submitted in ASCII format via EFS-Web and is hereby incorporated by reference in its entirety. Said ASCII copy, created on Mar. 15, 2011, is named MALBOOBI.txt and is 11,638 bytes in size.

Iranian National Science Foundation sponsors the present invention for international filing.

BACKGROUND

1. Technical Field

The embodiments herein generally relate to enzymes of APases family. The embodiments herein more particularly relate to nucleic acid sequences coding for novel APases enzymes family.

2. Description of the Related Art

During the last two decades, APases including phytases have attracted considerable attention for both research and industrial applications in the areas of nutrition, environmental protection and health.

Monoesteric phosphatases (EC 3.1.3) commonly known as acid phosphatases (APases), catalyze the hydrolysis of phosphoric ester bonds of various substrates including phosphorylated sugars, lipids, proteins and nucleotides (Boyer et al., 1961). These enzymes are encoded by a highly diverse set of genes. Thaller and colleagues (1998) placed prokaryotic non-specific APases (NSAP) in three distantly related families A, B and C on the basis of shared conserved motifs despite of lack of overall sequence similarities. NSAPs are secreted enzymes which are produced as soluble periplasmic proteins or as membrane-bound lipoproteins, which are usually able to dephosphorylate a broad range of substrates and exhibit optimal catalytic activity at acidic to neutral pH values. Class A encompasses a group of bacterial APases which have a molecular mass around 25 kDa and carry a signature sequence motif defined as GSYPSGHT (SEQ ID NO: 9). Class B APases contain a polypeptide with a molecular mass of approximately 25 kDa for which FDIDDTVLFSSP (SEQ ID NO: 10) could be proposed as family motif sequence. Class C NSAP are a group with a molecular mass around 30 kDa and share four conserved aspartate residues. At the sequence level, class C enzyme appear to be related, although distantly, to class B and also to some plant acid phosphatases. Because of the presence of four invariant aspartate (D) residue within the most conserved domain among class B and C bacterial NSAPs and some plant APases, Rossolini and coworkers (1998) proposed a superfamily of DDDD (SEQ ID NO: 11) phosphohydrolyses.

Considering much higher sequence diversity in eukaryotic APases, Feizi and Malboobi classified plant APases into five distinct families with almost no similarities among them, even among the conserved family motifs. Considering the whole set of known APases in *Arabidopsis thaliana* and *Oryza sativa* as representatives of the dicotyledonous and monocotyledonous plants, the defined families were named as purple APase (PAP), Histidin APase (HAP), haloacid dehalogenase related APase ((HAD)-HRP), phospholipid APase (PLP) and SurE APase (SAP) families based on specific criteria and sequence similarities within them. These researchers proposed that the necessity for phosphate homeostasis for cellular survival has been the selective force which favored structural adaptations of various superfamily members toward APase activity to target as many alternative substrate types as possible. Then, divergent evolution within the families allowed broadening of substrate subtypes. For instance, these analogous families encompass four types of known phytase enzymes: HAP, PAP, cystein APase (CP) and a prokaryotic one named β-propeller phytase or BPP that are distinct both in terms of amino acid sequence and tertiary structure (Lung et al., 2008; Mullaney and Ullah 2005).

With respect to the important agricultural and industrial applications of APases, isolation of relevant genes has been of great interest and several gene isolation methods have been utilized.

A subset of these enzyme, named phytase, belongs to a special class of phosphomonoesterases [myo-inositol hexakisphosphate phosphorylase] and is capable of initiating the stepwise release of phosphate from phytate [myo-inositol (1, 2, 3, 4, 5, 6) hexakisphosphate], the major storage form of phosphate in plant (Greiner et al., 2002). For instance, phytases are now used as an animal feed additive to assist digestion of plant material for simple-stomached animals by liberating phosphate (Cromwell et al., 1995; Igbasan et al., 2001; Leesen et al., 2000; Simons et al., 1990; Miksch et al., 2002). The inorganic phosphate supplementation in the diets for simple-stomached animals can be reduced by including adequate amounts of phytase, and as a result, the fecal phosphate excretion of these animals can be reduced by as much as 50% (Arjula et al., 2009). Therefore, the utilization of phytase enzyme has been proposed as a means to reduce the level of phosphate pollution in the residuals of industries involving intensive animal production such as poultry or fish.

APases have a wide distribution in plants, microorganisms and also in some animal tissues (Greiner et al., 1993; Dvorakova 1998; Konietzny and Greiner 2002). Recent research has shown that microbial APases are the most promising ones for biotechnological application in terms of cost, ease of production and processing (Pandey et al., 2001). APases have been detected in various bacteria, such as *Bacillus* sp. (Choi et al., 2001; Kerovuo et al., 1998; Kim et al., 1998; Shimizu 1992), *Pseudomonas* sp. (Irving and Cosgrove 1971; Richardson and Hadobas 1997), *Pseudomonas syringae* (Cho et al. 2003), *Escherichia coli* (Golovan et al. 2000; Greiner et al. 1993), *Enterobacter* (Yoon et al., 1996), *Klebsiella* sp. (Greiner et al., 1997), *Citrobacter braakii* (Kim et al., 2003), *Lactobacillus sanfranciscensis* (De Angelis et al. 2003), *Pantoea agglomerans* (Greiner 2004) and *Pseudomonas putida* (Malboobi et al., 2009). Also, several bacterial phytase-encoding genes have been cloned from *Bacillus* sp. (Kim et al., 1998), *Escherichia coli* (Rodriquez et al., 1999; Golovan et al., 2000), *Klebsiella* sp. (Sajidan et al., 2004), *Obesumbacterium proteus* (Zinin et al., 2004), *Pseudomonas syringae* (Cho et al., 2005), *Yersinia intermedia* (Huang et al., 2006), and *Citrobacter* sp. (Luo et al., 2007). For lactic acid bacteria, however, the results were inconsistent; a few strains seem to have a quite low phytase activity, while for the majority of strains no phytase activity was detected. Recently it was shown that lactic acid bacteria isolated from sourdoughs exhibited a considerable phytate degrading capacity (De Angelis et al., 2003). Among the different lactic acid bacterial strains isolated from sourdoughs, *Lactobacillus sanfranciscensis*, which is considered as a key sourdough lactic acid bacterium, was identified as the best phytase producer. The APases produced by fungi are extracellular, whereas the enzymes from bacteria are mostly cell associated. The only bacteria showing extracellular phytase activity are those of the genera *Bacillus* and *Enterobacter*. The APases of *Escherichia coli* have been reported to be periplasmatic enzymes and phytase activity in *Selenomonas ruminantium* and *Mit-*

*suokella multiacidus* was found to be associated with the outer membrane (D'Silva et al., 2000).

Apart from fungi and bacteria, APases including phytase have been isolated and characterized from cereals such as triticale, wheat, maize, barley and rice and from beans such as navy beans, mung beans, dwarf beans and California small white beans that generally have lower enzyme activities than the bacterial ones. In general, legumes and oilseeds exhibit a 10-fold lower activity compared to cereals (Vohra and Satyanarayana 2003; Konietzny and Greiner 2002).

Since certain APases have preferred substrate ranges (Shamsuddin 2002, Vucenik et al., 2003, Oh et al., 2004), APases may find biotechnological applications in food processing to improve meal quality in particular for the reduction of phytate contents in feed and food (Lei et al., 2001; Vohra and Satyanarayana 2003; Haefner et al., 2005), in diagnostic kits as an stable, strong indicator enzyme and in mining industry as bioleaching agent. Depending on the application, an APase in which there is commercial interest, certain criteria should be met. Enzymes used as feed additives should be effective in releasing phosphates from phytate in the digestive tract, stable to resist inactivation by heat from feed processing and storage, and cost-effective for production. Thermo stability is a particularly important issue since feed pelleting is commonly performed at temperatures between 65° C. and 95° C. Although an after-spray apparatus for pelleted diets and/or chemical coating of phytase may help by passing the hot steps, thermostable phytases are still better candidates for feed supplements (Arjula et al., 2009).

So far naturally occurring APases having the required level of thermo stability for application in animal feed have not been found in nature (Lei et al., 2001). Up till now, two main types of APases have been identified; acid APases with an optimum pH around 5.0 and alkaline APases with an optimum pH around 8.0 (Oh et al., 2004). Most of the so far described microbial APases belong to the acidic ones and their pH optima range from 4.0 to 5.5.

Due to the shortage in nonrenewable resources of phosphorus, costs of production and environmental pollution concerns, there is a great desire to utilize APases, particularly in the area of food and feed production. Such enzymes must possess certain criteria for industrial applications such as high specific activity, thermo stability and activity in a broad range of pH. Hence there is a need for a cost effective and competitive production of APases with high yield, high specific activity and required purity level for desired industrial applications.

The above mentioned shortcomings, disadvantages and problems are addressed herein and which will be understood by reading and studying the following specification.

OBJECTIVES OF THE EMBODIMENTS

The primary object of the embodiments herein is to provide a recombinant APases enzyme encompassing a phytase and a sugar phosphatase.

Another object of the embodiments herein is to provide a recombinant APases enzyme which is active at high temperature and at a broad range of pH to withstand the harsh conditions of food processing and digestive system of animals.

Yet another object of the embodiments herein is to provide a recombinant APases enzyme which can be used in a variety of processes requiring conversion of phosphate compounds to release inorganic phosphate such as in fertilizing plants, poultry, dairy, fishery and human food.

Yet another object of the embodiments herein is to provide recombinant APases enzyme which does not match any of the previously described prokaryotic and eukaryotic APase families neither for the overall sequence nor for the shared motifs.

Yet another object of the embodiments herein is to provide a recombinant APases enzyme which shows divergence from major facilitator superfamily i.e. MFS family.

Yet another object of the embodiments herein is to provide a novel group of APases family.

Yet another object of the embodiments herein is to provide a rapid and efficient method for production of recombinant APases enzyme.

These and other objects and advantages of the embodiments herein will become readily apparent from the following detailed description taken in conjunction with the accompanying drawings.

SUMMARY

The various embodiments herein provide a novel family of APases encompassing a phytase and a sugar phosphatase that are active at high temperature and a broad range of pH, mainly in acidic condition, such that they can stand harsh conditions in food processing and in digestive system of animals. The APases is obtained from *Pseudomonas putida* strain P13 isolated from soil.

The embodiments herein provide recombinant APase nucleic acid sequences comprising SEQ ID NO: 1 and SEQ ID NO: 2. According to one embodiment herein, the SEQ ID NO: 1 encodes for a phytase enzyme and have an amino acid sequence according to SEQ ID NO: 3. According to another embodiment herein, the SEQ ID NO: 2 encodes for a sugar phosphatase enzyme and have an amino acid sequence according to SEQ ID NO: 4. The SEQ ID NO: 1 encodes for 249 amino acid residues while the SEQ ID NO: 2 encodes for 462 amino acid residues. The nucleic acid sequences are obtained from *Pseudomonas putida* strain P13. The optimum temperature for activity of the enzyme is 20° C. to 75° C. The optimum temperature for maximum activity is 60° C. The optimum pH for activity of the enzyme is 5. The molecular weight the phytase enzyme is 27 kDa with $K_m$ value as 0.237 mM and $V_{max}$ value as 0.281 mmol min$^{-1}$ mg$^{-1}$. The specific activity of the phytase enzyme is 281.7 Umg-1 of protein. The molecular weight of the sugar phosphatase enzyme is 50 kDa with $K_m$ value as 1.34 mM and $V_{max}$ value 0.466 mmol min$^{-1}$ mg$^{-1}$. The specific activity of sugar phosphatase enzyme is 466 Umg$^{-1}$.

According to one embodiment, a phytase and a sugar phosphatase comprises the amino acid sequence essentially according to SEQ ID NO: 3 and SEQ ID NO: 4.

According to one embodiment, a method to produce recombinant APases having an amino acid sequence essentially according to SEQ ID NOS: 3 & 4 being active at 60° C. and having optimum acidic pH for their activity. DNA sequences essentially according to SEQ ID NOS: 1 & 2 encoding amino acid sequences essentially according to SEQ ID NOS: 3 & 4 are digested from their corresponding vector and transferred into expression vectors which allow high expression of these genes. The newly cloned genes are expressed in prokaryotic or even eukaryotic hosts to produce active recombinant enzymes. The produced enzymes may be used intracellular or extracted from the cells to be used for hydrolysis of phosphate compounds.

According to one embodiment, a recombinant acid phosphatase (APase) composition for food and feed comprises a phytase wherein the phytase includes amino acid sequence according to SEQ ID NO: 3 and a sugar phosphatase wherein the sugar phosphatase includes an amino acid sequence according to SEQ ID NO: 4. The recombinant APase is active in a temperature range of 20° C.-75° C. and at a pH of 5, wherein an optimum temperature is 60° C. The SEQ ID NO: 3 includes at least 249 amino acid residues and wherein the SEQ ID NO: 3 is derived by encoding a SEQ ID NO: 1. The SEQ ID NO: 4 includes at least 462 amino acid residues and wherein the SEQ ID NO: 4 is derived by encoding a SEQ ID NO: 2. The SEQ ID NO: 1 and SEQ ID NO: 2 are obtained from *Pseudomonas putida* strain P13. The molecular weight of the phytase herein is 27 kDa and has a specific activity of 281.7 Umg$^{-1}$ whereas the molecular weight of the sugar phosphatase is 50 kDa having a specific activity of 466 Umg$^{-1}$.

According to one embodiment, a method of producing a composition of recombinant APases for food and feed wherein DNA sequences are first isolated from pseudomonas putida strain P13. Then, the DNA sequences are digested using a restriction enzyme. The digested DNA sequences are transferred to a vector. The transferred DNA sequences are expressed in a host and the recombinant APase is thus produced. The DNA sequences include SEQ ID NO: 1 & SEQ ID NO: 2, wherein the SEQ ID NO: 1 encodes for SEQ ID NO: 3 and wherein the SEQ ID NO: 2 encodes for SEQ ID NO: 4. The restriction enzyme includes EcoRI, SalI, or HindIII. The vector includes *Escherichia coli* DH5α, Bluescript KS$^-$ and pGEM-T easy vector. The host includes prokaryotic and eukaryotic cell.

According to one embodiment, a cloning strategy of a novel phytase gene obtainable from *Pseudomonas putida* strain P13 wherein the DNA sequence is essentially according to SEQ ID NOS: 1 & 2 which are isolated and cloned into various plasmid vectors.

These and other aspects of the embodiments herein will be better appreciated and understood when considered in conjunction with the following description and the accompanying drawings. It should be understood, however, that the following descriptions, while indicating preferred embodiments and numerous specific details thereof, are given by way of illustration and not of limitation. Many changes and modifications may be made within the scope of the embodiments herein without departing from the spirit thereof, and the embodiments herein include all such modifications.

BRIEF DESCRIPTION OF THE DRAWINGS

The other objects, features and advantages will occur to those skilled in the art from the following description of the preferred embodiment and the accompanying drawings in which:

FIG. 1 shows a nucleic acid sequence mentioned as SEQ ID NO. 1, according to one embodiment herein.

FIG. 2 shows a nucleic acid sequence mentioned as SEQ ID NO. 2, according to one embodiment herein.

FIG. 3 shows nucleic acid sequence mentioned as SEQ ID NO. 3, according to one embodiment herein.

FIG. 4 shows nucleic acid sequence mentioned as SEQ ID NO. 4, according to one embodiment herein.

DETAILED DESCRIPTION OF THE EMBODIMENTS

Figure 5:
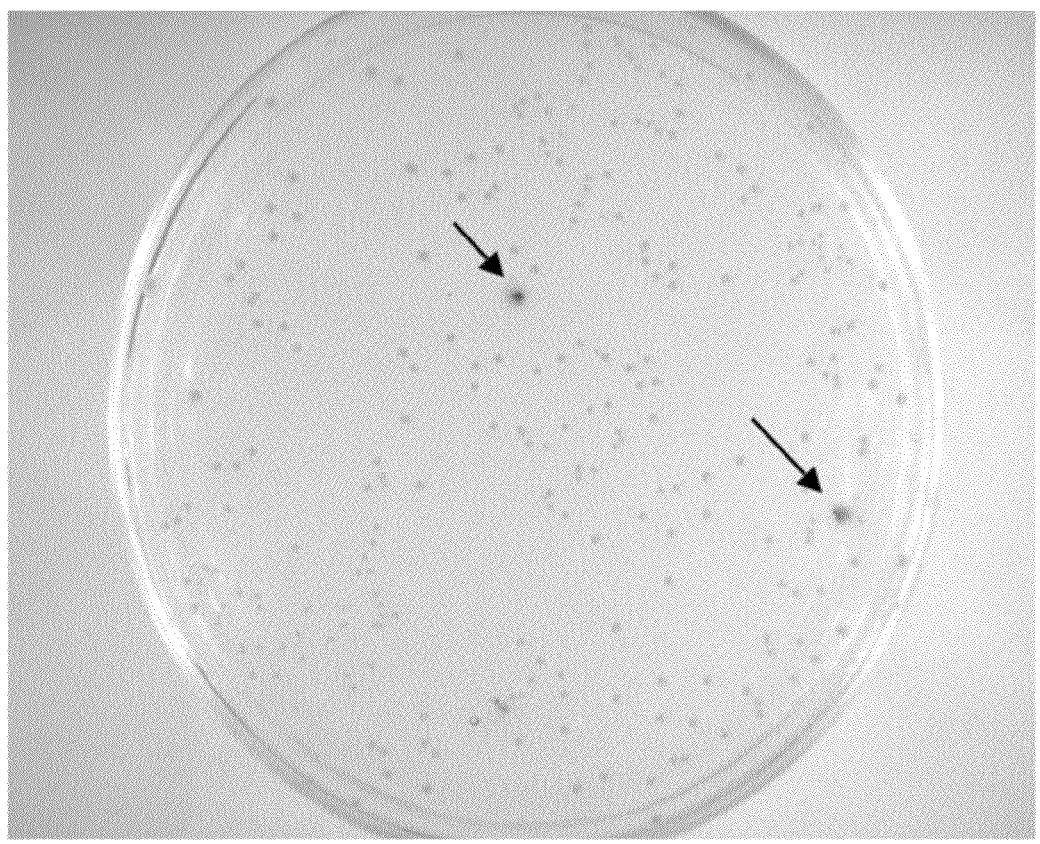
FIG. 5 shows a top view of a petridish containing BCIP medium showing the growth of two strong APase-expressing clones, according to one embodiment herein.

In the following detailed description, a reference is made to the accompanying drawings that form a part hereof, and in which the specific embodiments that may be practiced is shown by way of illustration. The embodiments are described in sufficient detail to enable those skilled in the art to practice the embodiments and it is to be understood that the logical, mechanical and other changes may be made without departing from the scope of the embodiments. The following detailed description is therefore not to be taken in a limiting sense.

The various embodiments herein relate to isolation and cloning of two novel DNA sequences from a bacterial strain (*P. putida* strain P13) encoding a novel family of APases including a phytase (myo-inositol hexakisphophate phosphodydrolyase) and a sugar phosphatase enzyme by functional screening of constructed genomic libraries. Phytase catalyses the hydrolysis of myo-inositol hexakisphosphate to inorganic phosphate and lowers myo-inositol phosphates and in some cases even myo-inositol. Similarly, sugar phosphatases hydrolyze a variety of sugar-phosphate compounds to their moiety plus a phosphate ion.

According to an embodiment, a recombinant acid phosphatase (APase) composition for food and feed comprises a phytase and a sugar phosphatase. The phytase includes an amino acid sequence according to SEQ ID NO: 3 and the sugar phosphatase includes an amino acid sequence according to SEQ ID NO: 4. The recombinant APase composition is active in a temperature range of 20° C.-75° C. and at a pH of 5. The recombinant APase composition has a maximum activity at an optimum temperature of 60° C.

The amino acid sequence according to SEQ ID NO: 3 includes 249 amino acid residues. The amino acid sequence according to SEQ ID NO: 3 is encoded by a nucleic acid sequence according to SEQ ID NO: 1. The nucleic acid sequence according to SEQ ID NO: 1 is obtained from *Pseudomonas putida* strain P13. The amino acid sequence according to SEQ ID NO: 3 has an activity for sodium phytase. The phytase has a molecular weight of 27 kDa with a Km value of 0.237 mM, a Vmax value of 0.281 mmol min$^{-1}$ mg$^{-1}$ and a specific activity of 281.7 Umg$^{-1}$.

The amino acid sequence according to SEQ ID NO: 4 includes 462 amino acid residues and the amino acid sequence according to SEQ ID NO: 4 is encoded by a nucleic acid sequence according to SEQ ID NO: 2. The nucleic acid sequence according to SEQ ID NO: 2 is obtained from *Pseudomonas putida* strain P13. The amino acid sequence according to SEQ ID NO: 4 has an activity for glucose-6-phosphate and D-Fructose-6-phosphate. The sugar phosphatase has a molecular weight of 50 kDa with a Km value of 1.34 mM, a Vmax value of 0.466 mmol min$^{-1}$ mg$^{-1}$ and a specific activity of 466 Umg$^{-1}$.

A method of producing a recombinant APase composition for food and feed involves isolating a DNA sequence from pseudomonas putida strain P13. The isolated DNA sequence is digested using a restriction enzyme. The digested DNA sequence is transferred to a vector. The transferred DNA sequence is expressed in a host to produce the recombinant APase.

The DNA sequence includes a nucleic acid sequence according to SEQ ID NO: 1 and a nucleic acid sequence according to SEQ ID NO: 2. The nucleic acid sequence according to SEQ ID NO: 1 encodes an amino acid sequence according to SEQ ID NO: 3 to obtain a phytase. The phytase includes the amino acid sequence according to SEQ ID NO: 3.

The nucleic acid sequence according to SEQ ID NO: 2 encodes an amino acid sequence according to SEQ ID NO: 4 to obtain a sugar phosphatase. The sugar phosphatase includes the amino acid sequence according to SEQ ID NO: 4.

The restriction enzyme is selected from a group comprising of EcoRI, SalI, and HindIII. The vector is selected from a group comprising of *Escherichia coli* DH5α, Bluescript KS– and pGEM-T easy vector. The host includes a biological cell. The biological cell is selected from a group comprising of prokaryotic cell and eukaryotic cell.

According to an embodiment herein, the novel DNA sequences (SEQ ID NO: 1 and SEQ ID NO: 2) are isolated and cloned from *P. putida* strain P13. The DNA sequences for a novel enzyme essentially has an amino acid sequence according to SEQ ID NO: 3 and SEQ ID NO: 4.

The isolated genes encoding APases described herein are grouped with major facilitator superfamily (MFS) members. MFS transporters are single-polypeptide secondary carriers capable of transporting small molecules including sugar phosphates. Pao and colleagues (1998) have classified members of MFS into 17 (or possibly 18) distinct families. These novel APases are grouped with family 12 and 14, known as sialate: H+ symporter (SHS) and Anion: Cation Symporter (ACS) family, respectively (for a review see Pao et al., 1998). The embodiments herein clearly show that the new members of MSF family i.e. the novel APases have phosphatase activity. Apparently, the embodiments herein describe a convergent evolution of APases through which some members of other protein families are neo-functionalized to enzymes that is essential for adaptation to harsh environmental conditions.

Biochemical analysis showed that while both have a broad substrate range, SEQ ID NO: 1 encoding SEQ ID NO: 3 has substrate preference for sodium phytate. The other novel gene, SEQ ID NO: 2 encoding SEQ ID NO: 4, hydrolyses glucose-6-phosphate and D-Fructose-6-phosphate at higher rates.

According to one embodiment herein, the phytase-encoding gene (SEQ ID NO:1 encoding SEQ ID NO:3) releases all phosphate molecules from phytate except for IP2 while myo-inositol pentakisphosphate is the final product of phytate dephosphorylation by the enzyme related to SEQ ID NO:2 encoding SEQ ID NO:4. All Known microbial acid phytate-degrading enzymes release five of the six phosphate residues of phytate to generating myo-inositol(2)monophosphate as the final product (Greiner et al., 2001; Sajidan et al., 2004; Wyss et al., 1999). Similarly, some APases encoding genes have been reported to be able to release only one of phosphates from phytate (Greiner 2004, Herter et al., 2006).

The embodiments herein are supported with following examples. The examples set forth are not meant to limit the scope in any manner.

EXAMPLE 1

Screening for Isolation of APase-Encoding Genes

*P. putida* strain P13 that produce strong APases activity was isolated from alkaline soils as a source of genomic DNA. *Escherichia coli* DH5α were isolated as the host for recombinant plasmids. Bluescript KS– plasmids were used for library construction and sub-cloning procedures. Moreover, production of recombinant enzymes and subsequent purification were carried out in pGEM-T easy vector. Basic recombinant DNA procedures were performed as described by Sambrook and Russell (2001).

Genomic library was constructed by complete or partial digestion of *P. putida* strain P13 genomic DNA with EcoRI, SalI or HindIII. The DNA fragments were ligated into digested and dephosphorylated pBluescript KS–, with T4 DNA ligase by overnight incubation at 22° C. The ligation mixture was used to transform *E. coli* DH5α cells by electroporation. Electroporation was carried out by Gene Pulser II (Bio-Rad). A single pulse of 1.8 kV was applied with a capacitance of 25 μF and resistance of 500 Ohm.

Screening for APase-encoding genes was performed on Sperber medium containing 50 mg/l BCIP (5-boromo 4-choloro 3-indolyl phosphate). Sperber medium consist of g/l: agar, 16; glucose, 10; Na-phytate, 2.5; yeast extract, 0.5; Cacl2, 0.10; MgSO4, 0.25; pH, 7.2 supplemented with 100 μg/ml ampicillin. Colonies of *E. coli* transformants were then plated onto the selective medium to screen for APase positive clones. The presence of APase activity was monitored by the intensity of blue stain of bacterial colonies.

FIG. 5 shows a petri dish containing BCIP medium showing the growth of two strong APase-expressing clones. With respect to FIG. 5, the arrows show two intensely blue-stained clones that appeared to carry the same APase-encoding genes later.

EXAMPLE 2

Sub-Cloning of Recombinant APases

By screening *P. putida* P13 genomic library, a number of APase positive (Pho+) clones were identified. Restriction maps were used to group the isolated clones. All open reading frames (ORFS) within the genomic clones were sub-cloned by either restriction digest or DNA amplification with specific primers.

Figure 6A:
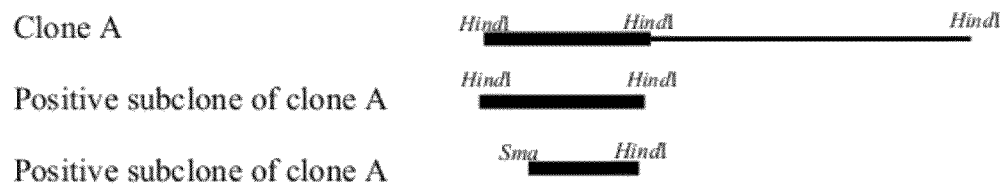
FIG. 6A shows the restriction map of the DNA inserts of the isolated clone A, according to one embodiment herein.
Figure 6B:
FIG. 6B shows the restriction map of the DNA inserts of the isolated clone B, according to one embodiment herein.

FIG. 6A shows the restriction maps of the DNA inserts of the isolated clone A. FIG. 6B shows the restriction maps of the DNA inserts of the isolated clone B. With respect to FIGS. 6A and 6B, the thick bars show the sub-cloned fragments carrying APase-encoding genes. Initial sizes of clone A and B were 8 and 7 kb, respectively. The open reading frames within the sub-cloned fragments, with the length of 1.5 and 2.4 Kb, encode proteins with high APase activities.

The PCR fragments were cloned into pGEM-T easy vector prior to transformation of E. coli DH5α and plated on Sperber medium containing BCIP as shown in EXAMPLE 1.

The sequence encompassing only ORF responsible for phytase activity of clone A was amplified with specific primers (5' GAA TTC ATG GCC TTT CAC CCA AT 3' SEQ ID NO: 5) and 5' AAG CTT TCA ACG TGC CCG CCG 3' (SEQ ID NO: 6)). Similarly, ORF corresponding to gene encoding a sugar APase within clone B was amplified by the use of specific primers (5' GAA TTC ATG AGC GGA TTC CAG AAG 3' (SEQ ID NO: 7) and 5' AAG CTT TCA CGC CTG GGC AGG G 3' (SEQ ID NO: 8)). The PCR products were ligated into pGEM-T easy vector. Transformation of the competent E. coli cells was done by freeze and thaw for which 100 mg of ligation mix was added. The suspension was carefully mixed with pipette tip and incubated on ice for 30 min. A heat shock at 42° C. for 45 sec was applied followed by incubation on ice for another 2 min. 800 μl of LB (lysogeny broth) was added and the bacterial suspension was incubated at 37° C. for 1 h. Aliquots of the suspension were spread evenly on LB supplemented with an appropriate antibiotic. The plates were incubated at 37° C. overnight. After 14 to 16 hrs, single colonies were picked and inoculated for plasmid mini preparation.

EXAMPLE 3

Phylogenetic Analysis of the Novel APases

BLASTX and/or BLASTP searches were performed in a non-redundant set of protein databases (Altschul et al., 1997) using the isolated nucleotide sequence and deduced amino acid sequences as queries.

Multiple sequence alignments of DNA and amino acid were carried out using Clustal W algorithm within MEGA 4.0 software package (Tamura et al., 2007). Phylogenetic trees for the retrieved APases were constructed by using Neighbor-Joining method. To do these, the phylogenetic relationship of the isolated sequences with each class of phytases (HAP, PAP, CP and BPP) or NSAPs (Class A, B and C) were assessed separately. As no significant similarity was found among them, then, representative sequences for each group were used to form dendrograms.

Figure 7A:
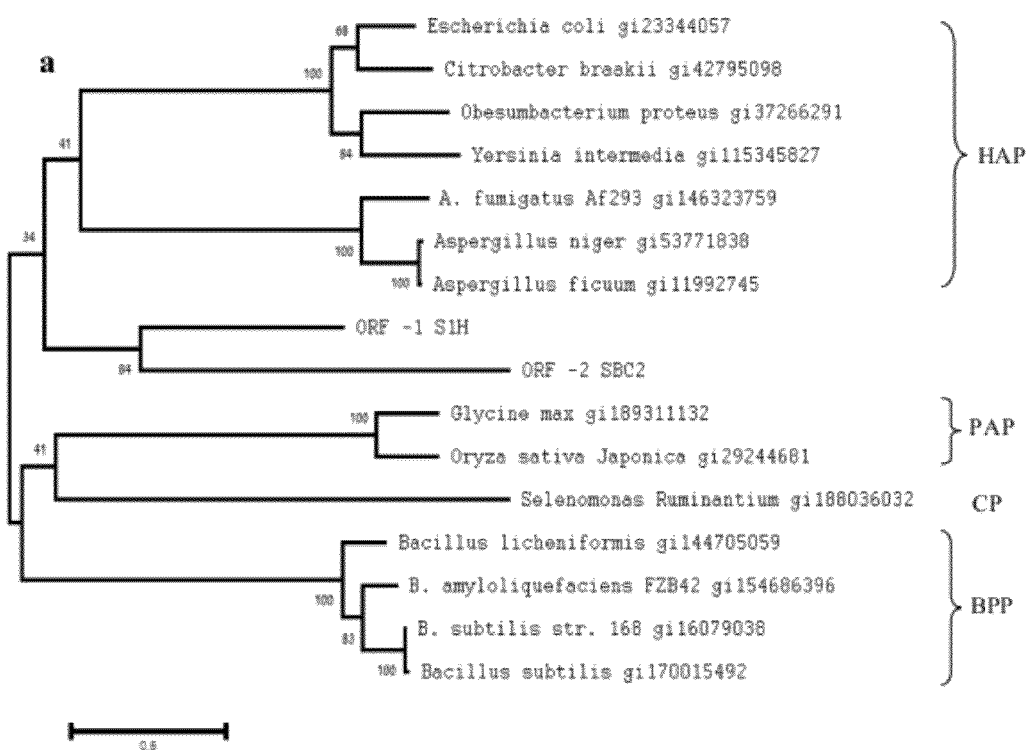
FIG. 7A shows dendrograms for clustering of bacterial phytase and APase sequences representatives in comparison to known phytase classes such as HAP, CP, PAP and BPP, according to one embodiment herein.

FIG. 7A show dendrogerams for clustering of bacterial phytase and APase sequences representatives in comparison to known phytase classes, HAP, CP, PAP and BPP. With respect to FIG. 7A, it shows that there is no relationship between the isolated APase-encoding genes from Pseudomonas putida and known phytase classes, HAP, CP, PAP and BPP.

Figure 7B:
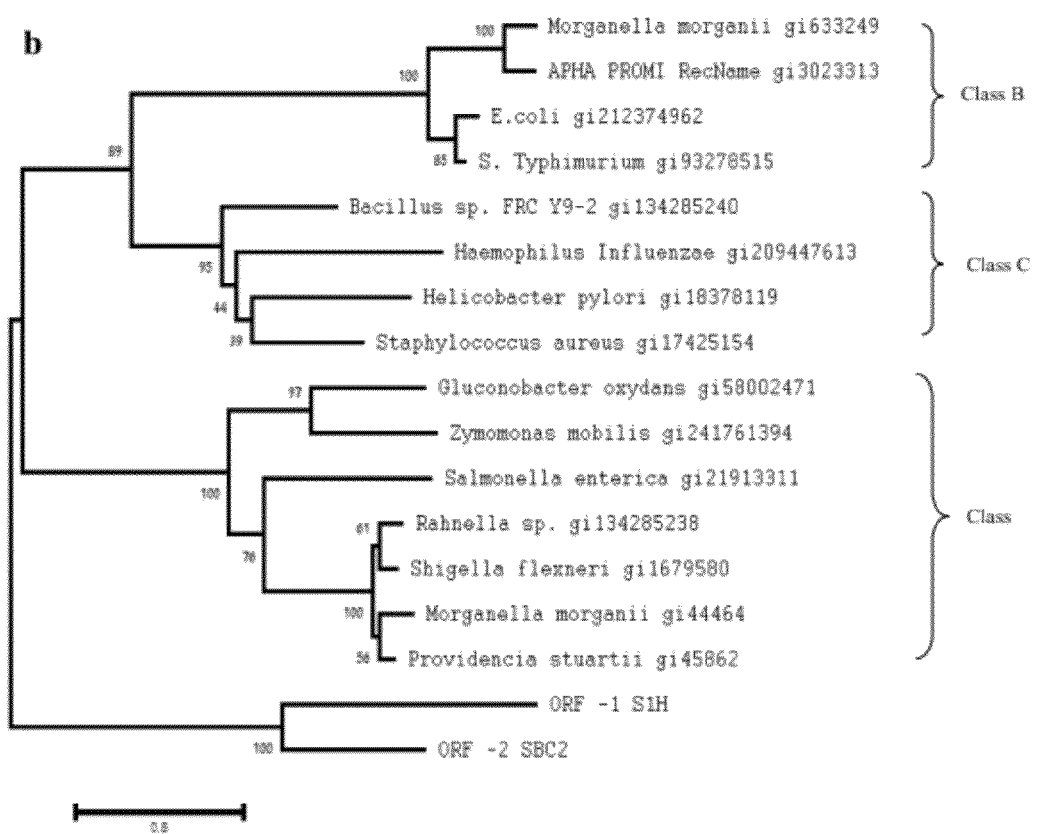
FIG. 7B shows dendrograms for clustering of bacterial phytase and APase sequences representatives in comparison to known NSAPs classes such as A, B and C, according to one embodiment herein.

FIG. 7B show dendrogerams for clustering of bacterial phytase and APase sequences representatives in comparison to known NSAPs classes A, B and C, according to one embodiment herein. With respect to FIG. 7B, it can be seen that there is no relationship between the isolated APase-encoding genes from Pseudomonas putida and NSAPs classes A, B and C. The isolated APase-encoding genes fall into a separate group when compared to the known phytases and NSAP classes.

Multiple sequence alignments of DNA and amino acid and subsequent phylogenetic analyses indicated that the isolated APase-encoding genes have no sequence similarities with either the known phytase classes (HAP, PAP, CP and BPP) or with the NSAPs (Class A, B and C). Although some biochemical features such as optimum pH and temperature of the isolated genes is similar to HAPs and NSAPs class A, there is no similarity for their amino acid sequence and even for the known motifs such as RHGXRXP (SEQ ID NO: 12) and GSYPSGHT (SEQ ID NO: 9), respectively.

Alternatively, the isolated genes encoding APases described in the embodiments were grouped with families 12 and 14 belong to MFS family known as sialate H+ symporter (SHS), and anion-cation symporter (ACS).

Figure 8:
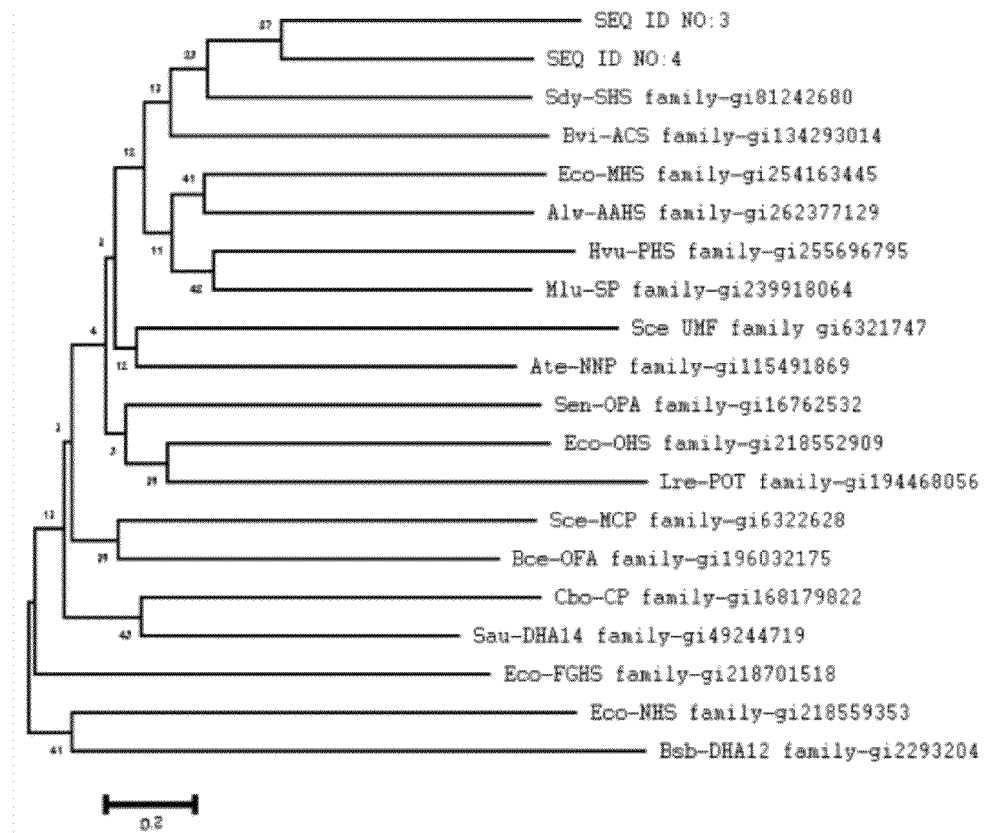
FIG. 8 shows clustering of novel APases with representatives of 18 families belonging to MFS, according to one embodiment herein.

FIG. 8 shows clustering of novel APases with representatives of 18 families belonging to MFS. With respect to FIG. 8, each data in phylogenetic tree consist of the name of bacteria, MSF subfamily and gene identification. The positions of the two proteins encoded by the isolated gene, SEQ ID NO: 3 and SEQ ID NO: 4 indicate high similarity with the family 12, sialate H+ symporter family and the family 14, anion-cation symporter family, respectively.

Data presented clearly show that the new members of MSF family have phosphatase activity. Apparently, this is another case of convergent evolution of APases through which some members of other protein families are neo-functionalized to enzymes that is essential for adaptation to harsh environmental conditions.

EXAMPLE 4

Expression and Purification of the Recombinant APase Enzymes Cell Growth and Lysis Positive transformant E. coli colonies containing pGEM-T easy vector carrying either SEQ ID NO: 1 or 2 were picked and grown at 37° C. in LB medium supplemented with 100 μg/l ampicillin for 16 hrs. The culture was then re-inoculated into fresh LB medium (1:100 dilutions) containing 100 μg/l ampicillin and grown aerobically at 37° C. After 20 hr of incubation, cells were harvested by centrifugation at 10,000 rpm and 4° C. for 15 min.

To purify the recombinant enzymes, the bacteria were lysed by the following procedure: (1) cells were repeatedly frozen at −80° C. for 10 min and thawed at room temperature for 20 min for three times before re-suspending in 20 mM sodium acetate buffer, pH 5.0; (2) cell walls were broken down further by addition of 10 mg/ml lysosyme and incubating for 3 h at room temperature; (3) cell rupture by sonication for 1 min which was repeated five times on ice. Cell debris was removed by centrifugation at 15,000 rpm and 4° C. for 30 min and the supernatant was used for enzyme purification by FPLC (Pharmacia FPLC System 500, Pharmacia, Uppsala, Sweden) run at a flow rate of 1 ml/min and 25° C.

Mono S HR 5/5 Chromatography

The dialyzed supernatant of previous step in 20 mM sodium acetate buffer with pH 5.0 was loaded onto a Mono S HR 5/5 column equilibrated with 20 mM sodium acetate buffer having pH 5.0. The column was washed with the same buffer for 30 min and then with a gradient consisting of 0-1 M NaCl in 20 mM sodium acetate buffer with pH 5.0 for 100 min. Two ml fractions were collected and those containing APase activity were pooled.

Sephacryl Chromatography

The APase activity-containing fractions from the previous step were loaded onto a 16/60 Sephacryl S-200 HR column equilibrated with 20 mM sodium acetate buffer having pH 5.0 and containing 0.2 M NaCl. The maximum loading volume per nm was 1 ml.

EXAMPLE 5

Molecular Size Estimation of the Novel APase Enzymes

To estimate the molecular mass of the APase enzymes, the purified proteins were gel-filtered on 16/60 Sephacryl S-200 HR equilibrated with 20 mM sodium acetate buffer having pH 5.0 containing 0.2 M NaCl. The column was calibrated with glucose-6-phosphate dehydrogenase (Mr=120,000), creatine kinase (Mr=81,000), bovine serum albumin (Mr=68,000), b-lactoglobulin (Mr=40,000) and myoglobin (Mr=17,000).

Sodium dodecyl sulfate polyacrylamide gel electrophoresis (SDS-PAGE) was performed according to Laemmli (1970) using a 10% acrylamide gel. Gels were stained by Coomassie brilliant blue G-250.

Figure 9A:
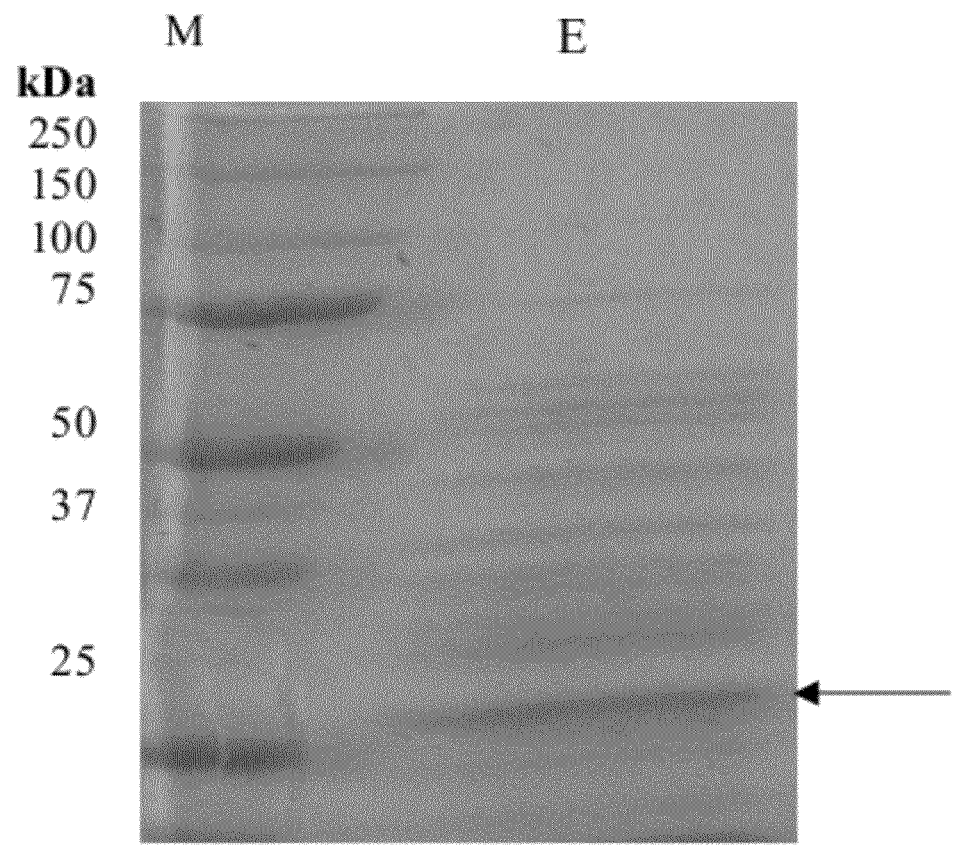
FIG. 9A shows a protein band of Sodium dodecyl sulfate polyacrylamide gel electrophoresis (SDS-PAGE) for phytase, according to one embodiment herein.
Figure 9B:
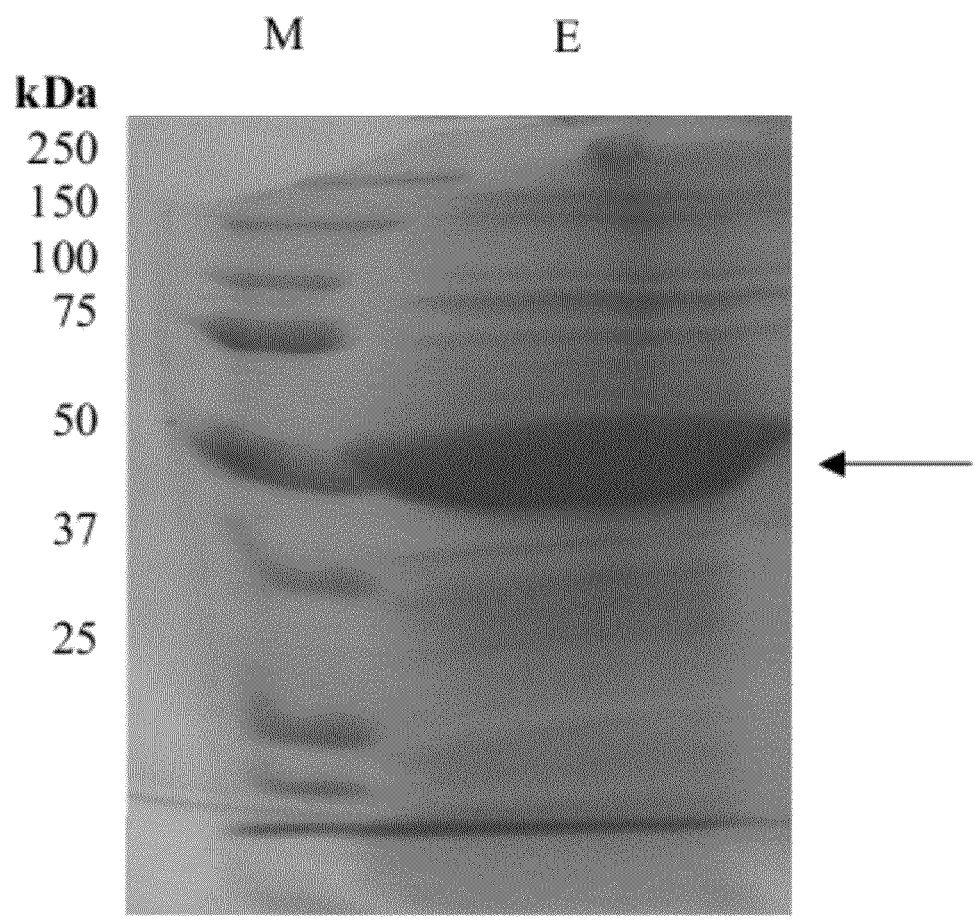
FIG. 9B shows a protein band of Sodium dodecyl sulfate polyacrylamide gel electrophoresis (SDS-PAGE) sugar phosphatase, according to one embodiment herein.

FIG. 9A shows a protein band of Sodium dodecyl sulfate polyacrylamide gel electrophoresis (SDS-PAGE) for phytase. FIG. 9B shows a protein band of Sodium dodecyl sulfate polyacrylamide gel electrophoresis (SDS-PAGE) sugar phosphatase. With respect to FIGS. 9A and 9B, M and E represent protein markers and semi-purified proteins, respectively.

Sequence analysis reveals that ORF within SEQ ID NO: 1 encodes a protein with of 249 residues as shown in SEQ ID NO: 3 and a calculated molecular mass of 26.7 kDa. Gel filtration of the enzyme on a calibrated Sephacryl S-200 column gave an approximate molecular mass of 30000±1500 Da with elution position being measured by determination of the enzyme activity. The estimated molecular mass by SDS-PAGE was quite close to the calculated mass 27 kDa. With respect to FIG. 9A, for phytase which corresponds to SEQ ID NO: 3, the protein band appeared at 27-KD. Therefore, molecular weight of the novel recombinant phytase was assigned to 27 kDa.

Similarly, an ORF within SEQ ID NO: 2 were found to encode a protein with 462 amino acid residues and a calculated molecular mass of 50 kD as shown in SEQ ID NO: 4. With respect to FIG. 9B, the molecular mass and homogeneity of the enzyme preparation were shown by SDS-PAGE and gel filtration. Gel filtration of the enzyme on a calibrated Sephacryl S-200 column gave a molecular mass of 50000±1500 Da with elution position being measured by determination of enzyme activity. With respect to FIG. 9B, for sugar APase which corresponds to SEQ ID NO: 4, the protein band appeared at 50-KD. Accordingly, the estimated molecular mass by SDS-PAGE was 50 kDa.

EXAMPLE 6

Substrate Specificity

APase activity was determined at 37° C. in 350 µl of 100 mM sodium acetate buffer, pH 5.0, containing 5 mM of various substrates as described in Table 1. Table 1 shows the degradation comparisons of different substrates by the purified enzymes encoded by the genes described in the embodiments herein.

Table 1 show a list of different substrates

| S. No | Substrate | Activity (%) | Activity (%) |
|---|---|---|---|
| 1. | Glucose-6-phosphate | 20 ± 3.4 | 100 ± 9.1 |
| 2. | D-Fructose-6-phosphate | 17 ± 2.2 | 65 ± 9.6 |
| 3. | Beta-Glycero phosphate | 1.3 ± 0.2 | 1.6 ± 0.2 |
| 4. | 1-Naphthyl phosphate | 0.64 ± 0 | 2.6 ± 0.1 |
| 5. | 2-Naphthyl phosphate | 2.8 ± 2 | 7.2 ± 4 |
| 6. | p-Nitrophenyl phosphate | 14 ± 5 | 22 ± 4.3 |
| 7. | Pyridoxal phosphate | 2.92 ± 2 | 2 ± 0.3 |
| 8. | AMP | 0 | 0.64 ± 0.2 |
| 9. | ATP | 0.28 | 0 |
| 10. | NADP | 0.52 | 0 |
| 11. | GTP | 0 | 0 |
| 12. | Sodium phytate | 100 ± 6 | 20 ± 6 |

The enzymes were incubated in 100 mM acetate buffer (pH 5) containing 1.5 mM of each substrate at 37° C. for 30 min and the released orthophosphate was measured as described in the text. The highest values for the preferred substrates, sodium phytate and glucose-6-phosphatase, were assigned as 100 percent. Each data point represents mean±SD of duplicate assay. The middle and the last columns show activity data for SEQ ID NO: 3 and SEQ ID NO: 4, respectively.

The enzymatic reactions began by adding 10 µl of the purified enzymes to the assays. After incubating for 30 min at 37° C., the liberated phosphate was measured according to the ammonium molybdate method (Heinonen and Lahti, 1981) with minor modifications. 1.5 ml of a freshly prepared acetone ammonium molybdate (AAM) reagent consisting of acetone/5 N $H_2SO_4$/10 mM ammonium molybdate (2:1:1 v/v/v) and 100 µl 1.0 M citric acid were added to the assay mixture. Any cloudiness, if present, was removed by centrifugation prior to the measurement of absorbance at 355 nm. To calculate the enzyme activity, a calibration curve was produced over the range of 5-600 nmol phosphate (e=8.7 cm2/nmol). One unit of activity was defined as the amount of enzyme required to liberate 1 µmol phosphate per min at 37° C. Blanks were run by adding AAM solution prior to adding the enzyme. As shown in Table 1, both APases described in herein have a broad range of substrates. However, strong preference of sodium phytate was apparent for SEQ ID NO: 3 encoded by SEQ ID NO: 1. Two preferred substrates, glucose-6-phosphate and fructose-6-phosphate, for SEQ ID NO: 4 encoded by SEQ ID NO: 2 share a sugar moiety.

EXAMPLE 7

Biochemical Properties of the Recombinant APases

Enzyme kinetics studies performed on semi-purified enzyme samples by the assay of inorganic phosphate liberated from Na-phytate or glucose 6-phosphate for SEQ ID NO: 3 and 4, respectively. For the pH profile, enzyme activity was assayed using the following buffers: glycine-HCl, pH 2.0-3.5; sodium acetate-acetic acid, pH 3.5-6.0; Tris-acetate, pH 6.0-7.0; Tris-HCl, pH 7.0-8.

Figure 10A:
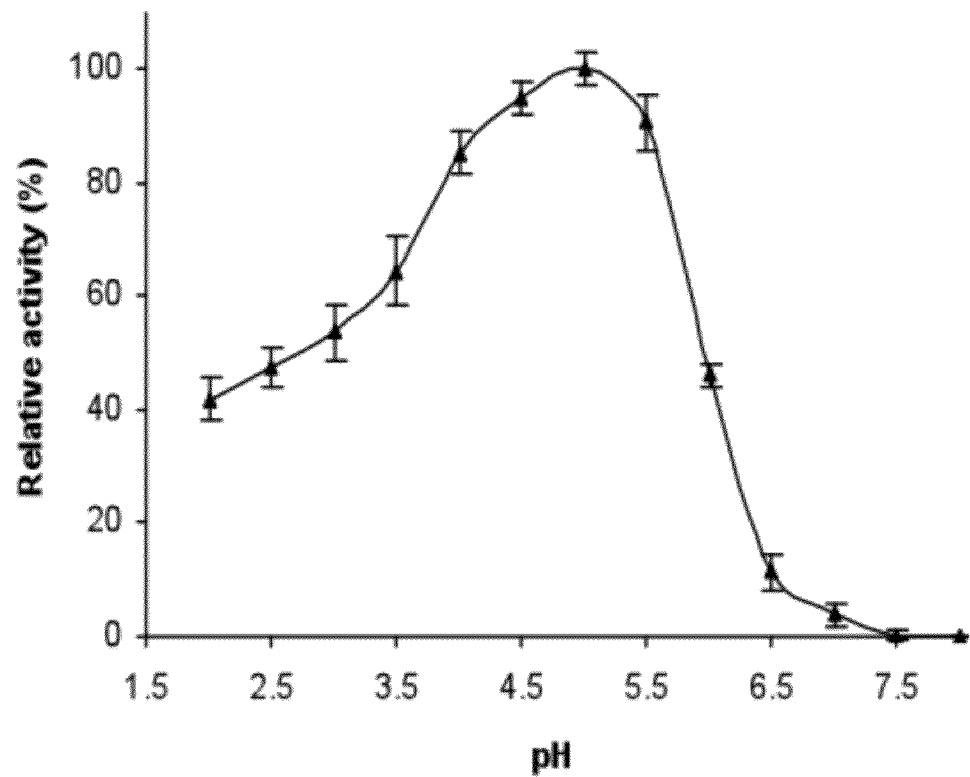
FIG. 10A shows a graph representing the activities of APase encoded by the isolated genes of phytase at different pH conditions, according to one embodiment herein.
Figure 10B:
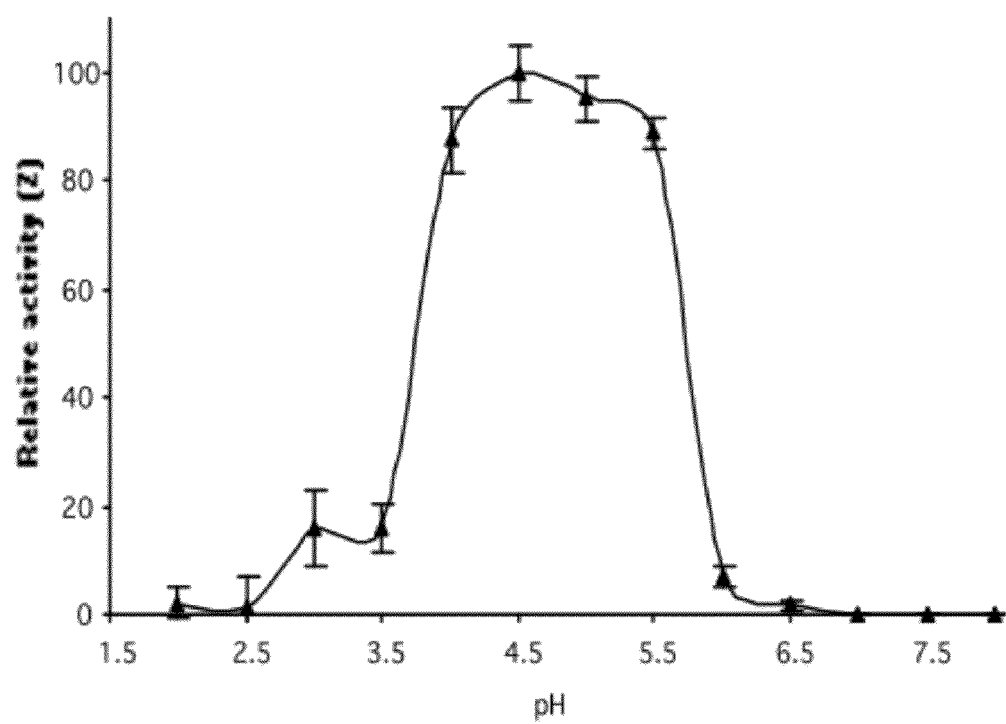
FIG. 10B shows a graph representing the activities of APase encoded by the isolated genes of sugar phosphatase at different pH conditions, according to one embodiment herein.

FIG. 10A shows a graph representing the activities (on y axis) of APase encoded by the isolated genes of phytase at different pH conditions (on x axis). FIG. 10B shows a graph representing the activities (on y axis) of APase encoded by the isolated genes of sugar phosphatase at different pH conditions (on x axis). Each data point represents mean±SD of duplicated assays. The activities of phytase (SEQ ID NO: 3) and sugar phosphatase (SEQ ID NO: 4) in various pH were assessed by using a series of buffering reagents at final concentration of 100 mM and 37° C. The activities were expressed by taking the maximum activity as 100 percent. From the figure, it is clear that the maximum activity was shown at a pH of 5. The optimal pH for activity of APase enzymes (SEQ ID NOS: 3 and 4) is 5.0.

Figure 11A:
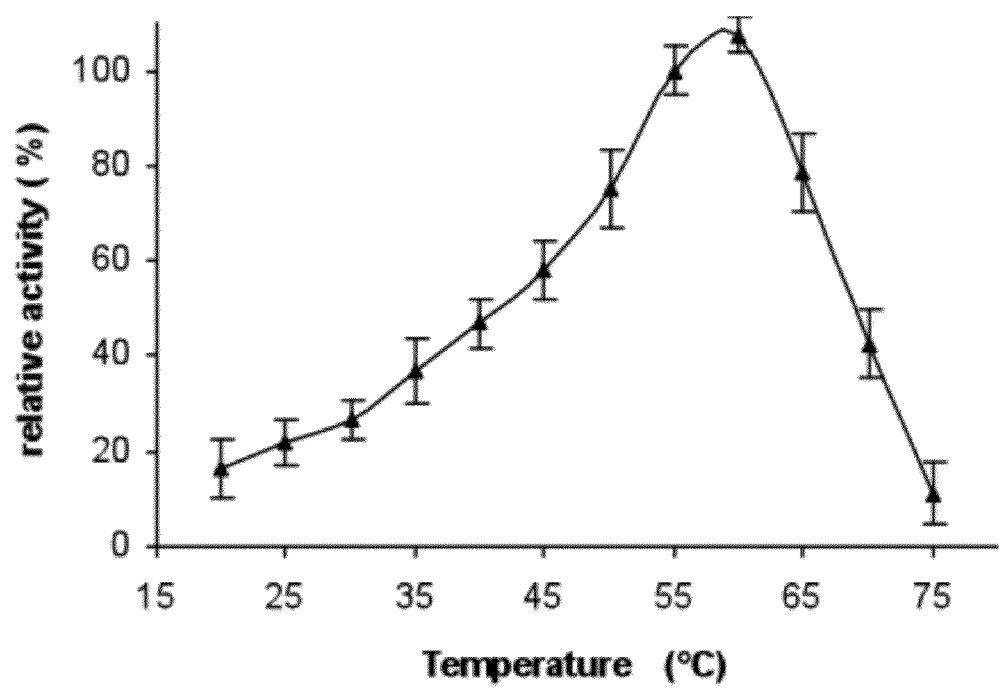
FIG. 11A shows a graph representing the activities of APase encoded by the isolated genes of phytase at different temperature conditions, according to one embodiment herein.
Figure 11B:
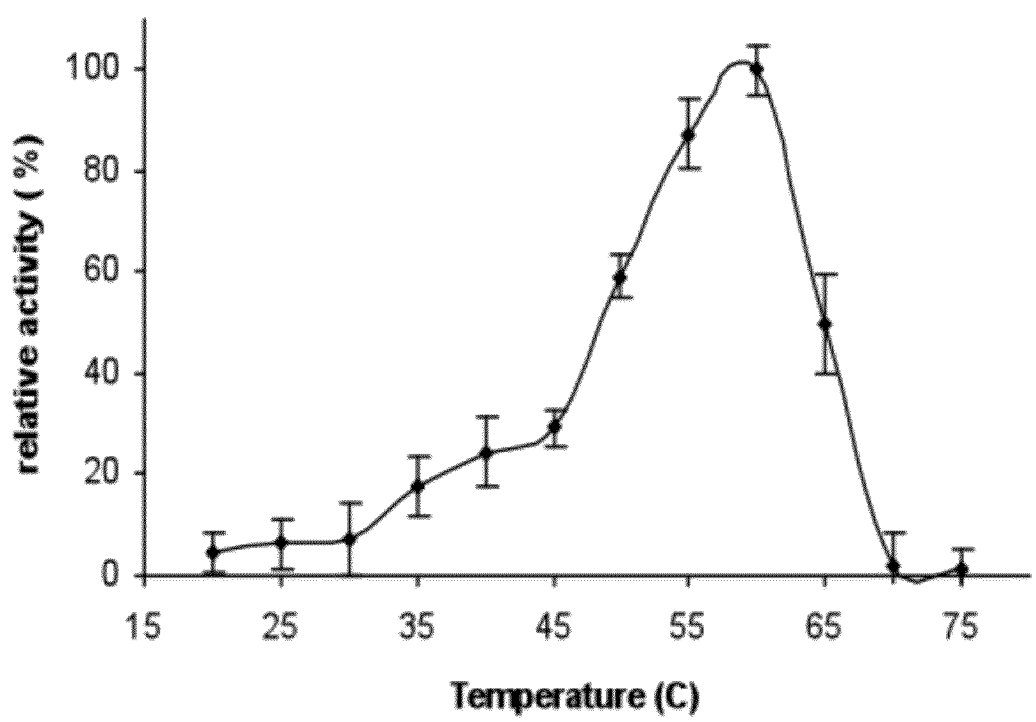
FIG. 11B shows a graph representing the activities of APase encoded by the isolated genes of sugar phosphatase at different temperature conditions, according to one embodiment herein.

FIG. 11A shows a graph representing the activities (on y axis) of APase encoded by the isolated genes of phytase at different temperature conditions (on x axis). FIG. 11B shows a graph representing the activities (on y axis) of APase encoded by the isolated genes of sugar phosphatase at different temperature conditions (on x axis). The optimum temperature was determined within temperatures ranging from 20° C. to 75° C. The optimal temperature for activity of APase enzymes (SEQ ID NOS: 3 and 4) is 60° C.

In order to determine the kinetic parameters of the APase enzymes expressed by isolated genes, $K_m$ and $V_{max}$ were estimated by measuring the release of the phosphate ion during hydrolysis using formation of a soluble phospho-molybdate complex in the AAM solution. The Km value is a measure of the affinity of the substrate for the enzyme wherein Vmax is the maximum velocity or rate at which the enzyme catalyzes a reaction. The kinetic parameters were calculated from a Lineweaver-Burke plot (Bisswanger 2002). For the hydrolysis of phytase (SEQ ID NO: 3) $K_m$ and $V_{max}$ were 0.237 mM and 0.281 mmol min$^{-1}$ mg$^{-1}$, respectively. The specific activity of the phytase was 281.7 Umg$^{-1}$ of protein. The purified recombinant protein of sugar phosphatase (SEQ ID NO: 4) displayed specific activity of 466 Umg$^{-1}$ protein against glucose-6-phosphate with a $K_m$ of 1.34 mM and a $V_{max}$ of 0.466 mmol min$^{-1}$ mg$^{-1}$.

EXAMPLE 8

Enzyme Thermal Stability

Enzyme stability was examined by the following procedure. Enzyme were treated at 25, 37, 40, 45, 50, 55, 60, 65, 70, 75, 80, 85 and 90 degree Celsius for 15 min prior to incubation at room temperature for 1 hour and assayed as described above. The activity of the recombinant phytase (SEQ ID NO:3) was not lost when incubated at various temperatures up to 55° C. while at 60, 65 and 70° C. only 36%, 9% and 3% of its activity was retained, respectively. No activity was detected when the reaction was pretreated at 80° C. or above. The enzyme activity of the recombinant sugar phosphatase (SEQ ID NO: 4) showed no significant difference up to 60° C. while with increasing temperature the enzyme activity decreased sharply suggesting a complete inactivation.

EXAMPLE 9

Degradation Pathway of APase Genes

In order to determine the pathway of phytate degradation and also the final product of enzyme degradation for the novel APases described in herein, time-coursed enzymatic reactions were carried out and the products were monitored on a high-pressure liquid chromatography (HPLC) column. The enzymatic reaction was started at 37° C. by addition of 50 μl of the purified enzyme. The enzymatic reaction was consisted of 350 μl 0.1 M sodium acetate buffer with pH 5.0 and containing 1.5 mM sodium phytate. 100 μl samples were removed periodically and the reaction was stopped by heat treatment (95° C., 10 min). Then, 20 μl of each sample was nm through HPLC column (column: Ultrasep ES100 RP18, Bischoff, Leonberg, Germany; HPLC: Pharmacia LKB LCC2252, Uppsala, Sweden) and peaks for each possible degradations product were identified by comparing to known myo-inositol phosphate standards as described by Sandberg and Ahderinne (1986).

HPLC analysis showed the difference between two APases described herein both in terms of the number and the order of hydrolysis of phosphate from phytate. HPLC analysis illustrated that the phytase-encoding gene (SEQ ID NO:1 encoding SEQ ID NO:3) released all phosphate molecules from phytate except for IP2 while myo-inositol pentakisphosphate is the final product of phytate dephosphorylation by the enzyme related to SEQ ID NO:2 encoding SEQ ID NO:4.

Although the embodiments have been described in some detail by way of illustration and example for the purposes of clarity of understanding, it is clearly not limited thereby and this invention encompass any changes and modifications that may be practiced within the scope of the appended claims by ones skilled in the art.

The foregoing description of the specific embodiments will so fully reveal the general nature of the embodiments herein that others can, by applying current knowledge, readily modify and/or adapt for various applications such specific embodiments without departing from the generic concept, and, therefore, such adaptations and modifications should and are intended to be comprehended within the meaning and range of equivalents of the disclosed embodiments. It is to be understood that the phraseology or terminology employed herein is for the purpose of description and not of limitation. Therefore, while the embodiments herein have been described in terms of preferred embodiments, those skilled in the art will recognize that the embodiments herein can be practiced with modification within the spirit and scope of the appended claims.

Although the embodiments herein are described with various specific embodiments, it will be obvious for a person skilled in the art to practice the invention with modifications. However, all such modifications are deemed to be within the scope of the claims.

It is also to be understood that the following claims are intended to cover all of the generic and specific features of the embodiments described herein and all the statements of the scope of the embodiments which as a matter of language might be said to fall there between.

What is claimed is:

1. A recombinant acid phosphatase (APase) composition for food and feed comprising: a phytase wherein the phytase comprises an amino acid sequence according to SEQ ID NO: 3; and a sugar phosphatase wherein the sugar phosphatase comprises an amino acid sequence according to SEQ ID NO: 4.

2. The composition according to claim 1, wherein the recombinant APase composition is active at a temperature range of 20° C.-75° C. and at a pH of 5, and wherein the recombinant APase composition has a maximum activity at an optimum temperature of 60° C.

3. The composition according to claim 1, wherein the amino acid sequence according to SEQ ID NO: 3 comprises 249 amino acid residues and wherein the amino acid sequence according to SEQ ID NO: 3 is encoded by a nucleic acid sequence according to SEQ ID NO: 1.

4. The composition according to claim 1, wherein the amino acid sequence according to SEQ ID NO: 4 comprises 462 amino acid residues and wherein the amino acid sequence according to SEQ ID NO: 4 is encoded by a nucleic acid sequence according to SEQ ID NO: 2.

5. The composition according to claim 3, wherein the nucleic acid sequence according to SEQ ID NO: 1 is obtained from *Pseudomonas putida* strain P13.

6. The composition according to claim 4, wherein the nucleic acid sequence according to SEQ ID NO: 4 is obtained from *Pseudomonas putida* strain P13.

7. The composition according to claim 3, wherein the amino acid sequence according to SEQ ID NO: 3 has an activity for sodium phytase.

8. The composition according to claim 4, wherein the amino acid sequence according to SEQ ID NO: 4 has an activity for glucose-6-phosphate and D-fructose-6-phosphate.

9. The composition according to claim 1, wherein the phytase has a molecular weight of 27 kDa with a $K_m$ value of 0.237 mM, a $V_{max}$ value of 0.281 mmol min$^{-1}$ mg$^{-1}$ and a specific activity of 281.7 Umg$^{-1}$.

10. The composition according to claim 1, wherein the sugar phosphatase has a molecular weight of 50 kDa with a $K_m$ value of 1.34 mM, a $V_{max}$ value of 0.466 mmol min$^{-1}$ mg$^{-1}$ and a specific activity of 466 Umg$^{-1}$.

* * * * *